United States Patent [19]
Williams

[11] Patent Number: 4,928,711
[45] Date of Patent: May 29, 1990

[54] HEAD IMMOBILIZER AND METHOD FOR IMMOBILIZING

[76] Inventor: Gary R. Williams, 943 Daisy Ave., Carlsbad, Calif. 92009

[21] Appl. No.: 443,563

[22] Filed: Nov. 29, 1989

[51] Int. Cl.⁵ .................. A61F 5/04; A61G 1/00; A47C 21/08
[52] U.S. Cl. .................. 128/869; 128/87 R; 128/870; 128/846; 5/82 R; 5/434; 5/436
[58] Field of Search .................. 128/87 R, 869, 870, 128/846; 5/82, 434, 436

[56] References Cited

U.S. PATENT DOCUMENTS

| | | | |
|---|---|---|---|
| 3,897,777 | 8/1975 | Morrison | 128/869 |
| 4,034,748 | 7/1977 | Winner | 128/87 |
| 4,182,322 | 1/1980 | Miller | 128/869 |
| 4,211,218 | 7/1980 | Kendrick | 128/87 |
| 4,297,994 | 11/1981 | Bashaw | 128/133 |
| 4,528,981 | 7/1985 | Behar | 128/133 |
| 4,571,757 | 2/1986 | Zolecki | 5/82 R |
| 4,584,729 | 4/1986 | Roberts et al. | 128/87 R X |
| 4,589,407 | 5/1986 | Koledin et al. | 128/869 |
| 4,594,999 | 6/1986 | Nesbitt | 128/87 R |
| 4,640,275 | 2/1987 | Buzzese | 128/133 |
| 4,710,991 | 12/1987 | Wilmore et al. | 5/434 X |
| 4,776,327 | 10/1988 | Russell | 128/87 R |

OTHER PUBLICATIONS

Stifneck HeadBed TM Advertisement, California Medical Products, Inc.
Apr. 1989 Advertisement—JEMS Magazine (Journal of the Emergency Medical Society).
Sep., 1988 JEMS Magazine, p. 20.
Two-page Head TM Vise Brochure—Lifestation 16.

*Primary Examiner*—Robert A. Hafer
*Assistant Examiner*—Kerry Owens
*Attorney, Agent, or Firm*—Frost & Jacobs

[57] ABSTRACT

There is provided a head immobilizer of the type which can be attached to a rigid backboard support, with the head immobilizer including a base and a pair of laterally extending side support panels. Each of these side support panels further comprises an inner panel and an outer panel, with the inner panel being conformable appropriately to a shape necessary to snugly support a head to be immobilized. The inner panel also includes an opening which effectively divides a portion of that inner panel into a pair of spaced inner support members extending laterally from the base. The outer panel has inner and outer edges, and is hingedly attached adjacent its inner edge to the inner panel such that it is foldable relative the inner panel to provide a substantially rigid brace for securing the inner panel in a desired immobilizing position. The outer panel also includes a cutout portion for providing substantial access to the opening of the inner panel when the inner panel is braced in a desired immobilizing position. The outer panel can be secured in a bracing position relative the inner panel, and the outer panel includes an attachment panel hingedly attached adjacent its outer edge for securing the outer panel in bracing position adjacent the base.

23 Claims, 4 Drawing Sheets

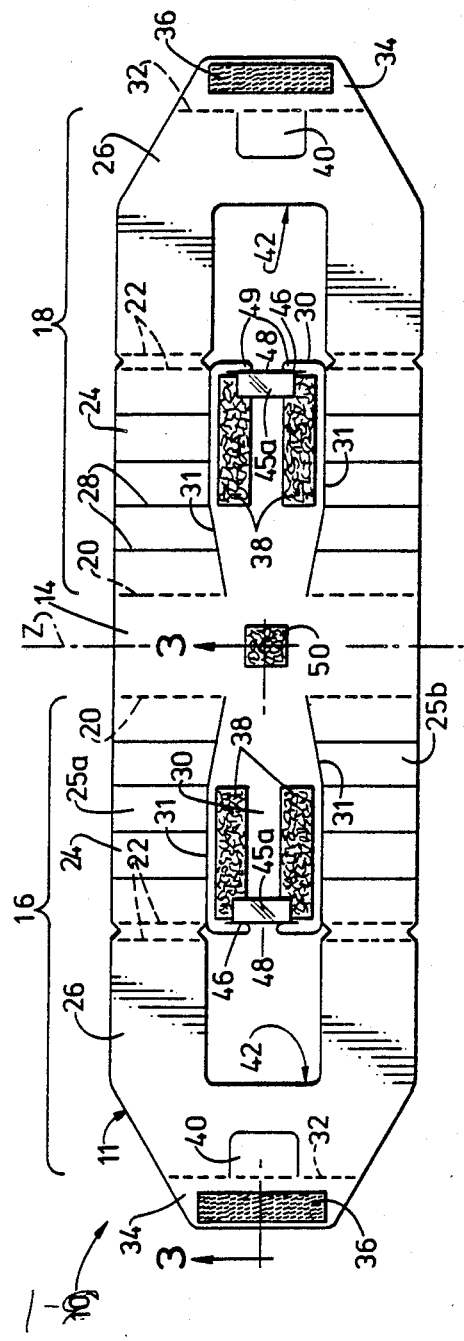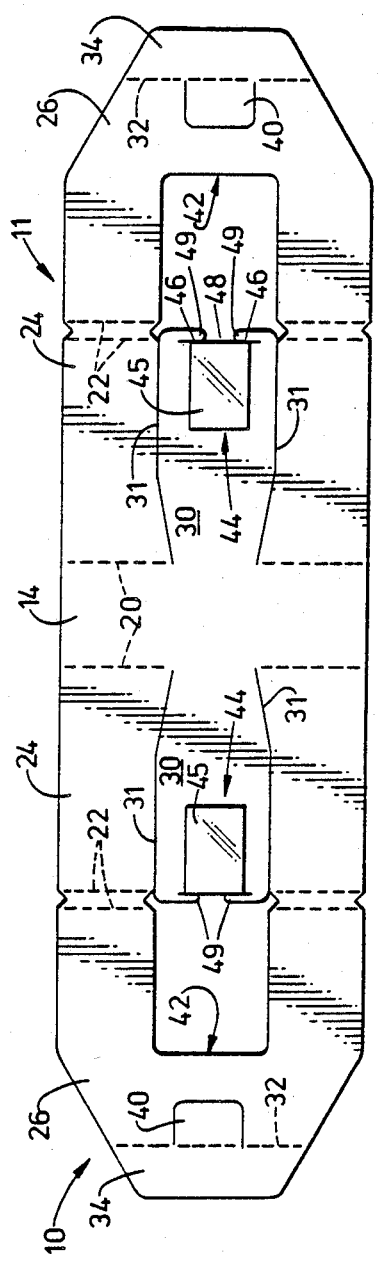

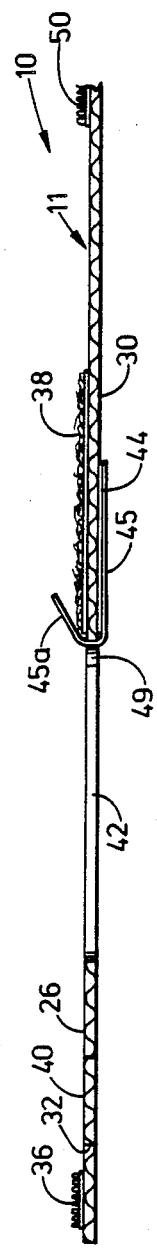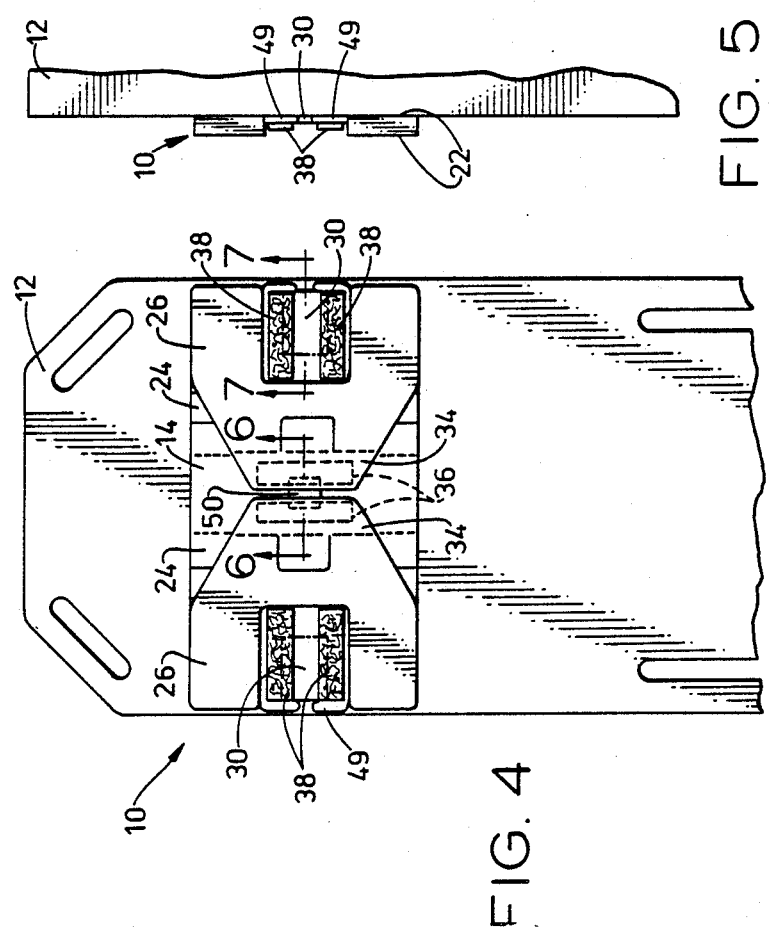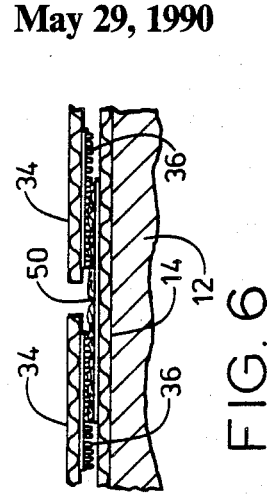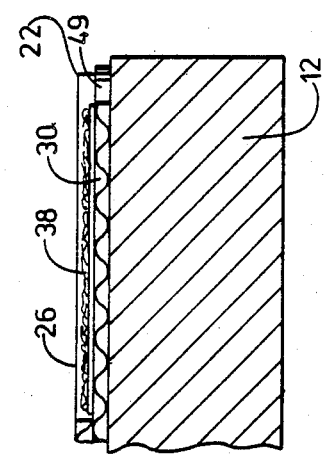
FIG. 3
FIG. 4
FIG. 5
FIG. 6
FIG. 7

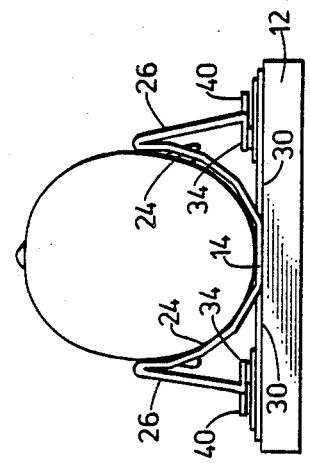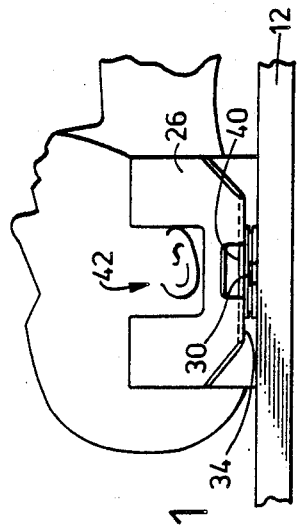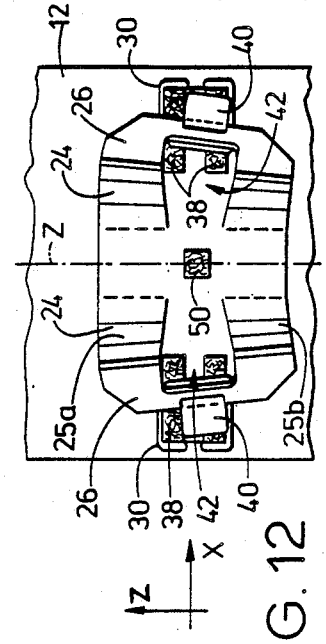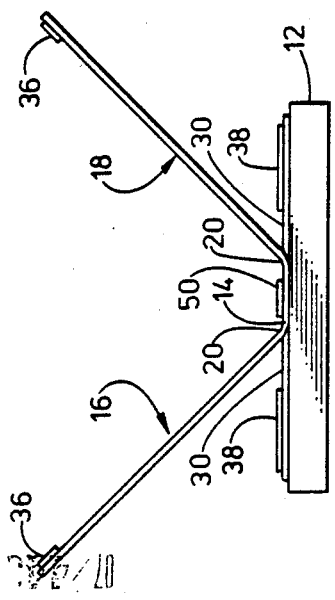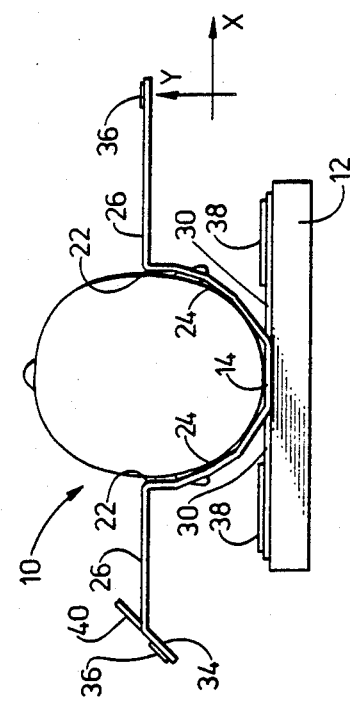
FIG. 10
FIG. 11
FIG. 12
FIG. 8
FIG. 9

HEAD IMMOBILIZER AND METHOD FOR IMMOBILIZING

TECHNICAL FIELD

The present invention relates to head or cervical immobilization devices, and more particularly, to an improved immobilizer and method for constraining the head and upper cervical portions of a person against movement during transport on a rigid support backboard.

BACKGROUND ART

Immobilization of the head and cervical portions of accident victims or those suspected of being exposed to cervical injuries, is often essential during transportation in order to minimize the possibility of further injury to the patient's spine or aggravation of injuries already suffered. A variety of spine, head and cervical immobilizing devices have been provided in the emergency medical industry over the years.

One form of head immobilizer is generally provided as an integral unit as part of a cervical spine immobilizing device often used independently of a rigid support backboard, and adapted to fit around the patient's body and cervical areas. Representative devices of this nature are shown in U.S. Pat. No. 4,034,748 (which issued to S. Winner on July 12, 1977), U.S. Pat. No. 4,211,218 (which issued to R. Kendrick on July 8, 1980), U.S. Pat. No. 4,589,407 (which issued to M. Koledin et al. on May 20, 1986), and U.S. Pat. No. 4,595,999 (which issued to W. Nesbitt on June 17, 1986). With the exception of the Koledin device, which was intended to be manufactured as a disposable device, the devices shown and described in these patents are relatively complex and expensive to manufacture, and are difficult to maintain and clean up between successive uses. Additionally, these devices do not address the specific problems of immobilizing a patient's head and cervical areas in conjunction with a rigid backboard unit. Consequently, additional devices are often required for proper immobilization after the patient is placed upon the rigid backboard.

A similar device directed to cervical immobilization is shown in U.S. Pat. No. 4,528,981, which issued July 16, 1985 to J. Behar. The Behar device is designed for use in association with a standard rigid backboard, and comprises a pair of resilient cylindrical head support rolls for location on opposite sides of a patient's head. The support rolls are attached to one another and held in place on the rigid backboard by straps which pass under the backboard and over the support rolls and the patient's head. However, the Behar rolls block access to the patient's ears and to a substantial portion of the head, and such access can be vital to monitoring the condition of the patient and the extent of the injuries. Additionally, the Behar device comprises a plurality of individual parts susceptible to misplacement or loss during periods of non-use, and requiring substantial storage space which is often at a premium in emergency medical areas and/or vehicles.

Other immobilization devices have been provided with pads or cushions designed to hold the patient's head in place in a manner similar to the Behar device described above. In particular, head restraint devices for use in conjunction with a rigid back support are shown in U.S. Pat. Nos. 3,897,777 (which issued to R. Morrison on Aug. 5, 1975, and 4,182,322 (which issued to L. Miller on Jan. 8, 1980). The Morrison head restraint is quite similar in operation to the Behar cervical immobilization device, with the exception that its pillows are attached at their lower edges by a trapezoidal web. The Morrison pillows are inflatable for use, and the patient's head is held in place between the pillow units by one or more overlying straps. The Morrison device, however, requires inflation of its pillows, or storage of the inflated pillows which would require substantial space, and includes various parts which can become misplaced between uses. Similarly, the Miller harness device is designed for use with a rigid backboard having a particularly shaped upper portion to facilitate attachment of the harness. As can be appreciated, the Miller device also comprises a plurality of individual parts. Both the Miller and Morrison devices prevent access to a substantial portion of the patient's head and cervical areas during use.

U.S. Pat. No. 4,571,757, which issued to D. Zolecki on Feb. 25, 1986, shows a head restraining device including a pair of L-shaped frames or brackets which can be removably fixed to the upper side of a rigid backboard. While the Zolecki device provides access to the patient's ears, its rigid construction does not provide for comfortable and snug conformance to a patient's head area, and the L-shaped brackets project substantially above the backboard and prevent convenient storage of the backboard with the immobilizer unit attached. If the Zolecki device is stored in attached position on a rigid backboard, it can become damaged by interaction with other structures; and if it is stored separately from the backboard, its individual parts can become lost and attachment of the device to the backboard will be required, wasting valuable time at the emergency scene.

U.S. Pat. No. 4,640,275, which issued to V. Buzzese et al. on Feb. 3, 1987, shows another attempt at providing a head restraint for use with rigid backboards. The Buzzese device, however, provides a pair of rigid side portions which do not conform to the patient's head and do not provide access to the patient's ears in use. Moreover, like the Zolecki device described above, the Buzzese restraint cannot be conveniently stored in a ready-to-use position on the rigid backboard.

Yet another device for immobilizing the cervical area of a patient is shown in U.S. Pat. No. 4,297,994, which issued to R. Bashaw on Nov. 3, 1981. The Bashaw immobilizer is similar to the Miller harness described above, as it calls for a complicated arrangement of pieces which includes cushions which substantially prevent access to the patient's ears in use.

More recently, simpler, disposable head support devices have been marketed under the trademark "HeadBed ™" by California Medical Products, Inc., and the mark "Head Vise ™" by Life Station 16 of Oklahoma. The HeadBed ™ device includes a base which slides under the patient's head and two support arms extending laterally from the base which extend upwardly above the patient's ears and conform to the upper portions of the patient's head. The support arms are held in place by attaching their distal end adjacent the rigid backboard support. While the HeadBed ™ provides access to the patient's ears, only minimal support is provided to the patient due to the location of the support arms only above the patient's ears. The Head Vise ™ is similar to the HeadBed ™ in that it provides a base portion having outwardly extending side support panels which conform to the patient's head. The Head Vise ™ provides better support for the patient's head, however, fails to provide access to the patient's ears as a result of its more substantial support arm portions. Additionally, the relatively wide support arm members of the Head Vise ™ do not readily conform to the generally tapered shape of the human head, and, therefore, cannot provide optimum support for a patient's head being immobilized in the device.

As can be seen from a review of the immobilizer devices available in the industry heretofore, a general problem with the immobilizer devices was that they were complex, expensive, and impractical to maintain, store, and clean between uses. The complex devices and their relative expense also made it impractical to discard the devices after only a single use. Additionally, the immobilizer devices generally did not provide access to the patient's ears, which can be vital to assessing injuries and providing proper medical assistance during transport and the like. More recent attempts to provide low costs, disposable immobilizer devices have failed to provide adequate support and immobilization, access to the patient's ears, and convenient storage on a rigid backboard support in a single unit. Additionally, immobilizers available in the industry have failed to provide optimum support of a patient's head and cervical region in conjunction with optimum comfort for the patient and accessibility for the medical service provider.

DISCLOSURE OF THE INVENTION

It is an object of the present invention to provide an improved head and cervical immobilizer device to address the problems and shortcomings of devices previously available.

It is also an object of the present invention to provide a head immobilizer device designed for use with a rigid backboard support and which can be conveniently stored in ready to use condition on that backboard support prior to use.

It is a further object of the present invention to provide an improved head immobilizer device which is simple to use, and which provides optimum support for a patient's head while providing substantial access to the patient's ears in use.

It is yet another object of the present invention to provide a single piece head immobilizer device which can be disposable in nature, which can be stored in a flat condition on a rigid back support, and which provides optimum support for a patient's head while providing substantial access to the patient's ears in use.

In accordance with one aspect of the present invention, there is provided a head immobilizer of the type which can be attached to a rigid backboard support, with the head immobilizer including a base and a pair of laterally extending side support panels. Each of these side support panels further comprises an inner panel and an outer panel, with the inner panel being conformable appropriately to a shape necessary to snugly support a head to be immobilized. The inner panel also includes an opening which effectively divides a substantial portion of that inner panel into a pair of spaced inner support members extending laterally from the base. The outer panel has inner and outer edges, and is hingedly attached adjacent its inner edge to the inner panel such that it is foldable relative the inner panel to provide a substantially rigid brace for securing the inner panel in a desired immobilizing position. The outer panel also includes a cutout portion for providing substantial access to the opening of the inner panel when the inner panel is braced in a desired immobilizing position. The outer panel can be secured in a bracing position relative the inner panel, and the outer panel includes an attachment panel hingedly attached adjacent its outer edge for securing the outer panel in bracing position adjacent the base.

BRIEF DESCRIPTION OF THE DRAWINGS

While the specification concludes with claims particularly pointing out and distinctly claiming the present invention, it is believed that the same would be better understood from the following description taken in conjunction with the accompanying drawings in which:

FIG. 1 is a plan view of the upper surface of a blank illustrative of an unassembled head immobilizer made in accordance with the present invention;

FIG. 2 is a plan view of the bottom surface of the immobilizer shown in FIG. 1;

FIG. 3 is an enlarged partial, cross-sectional view of the immobilizer of FIG. 1, taken along line 3—3 thereof;

FIG. 4 is a partial top plan view of the immobilizer of FIG. 1 shown in its folded state for storage and/or shipping and as mounted on top of a standard rigid support;

FIG. 5 is a side elevational view of the immobilizer attached to a rigid support as shown in FIG. 4;

FIG. 6 is an enlarged, partial cross-sectional view of the immobilizer of FIG. 4 taken along line 6—6 thereof;

FIG. 7 is an enlarged, partial cross-sectional view of the immobilizer of FIG. 4 taken along line 7—7 thereof;

FIG. 8 is a top end view of the immobilizer shown in FIGS. 1-4, showing the first step in erecting or deploying the head immobilizer from its storage or folded position, and illustrated particularly after the inner and outer side panels have been upwardly folded in an angled orientation relative the base of the immobilizer;

FIG. 9 is a view similar to FIG. 8, illustrating the next step in deploying the immobilizer from its folded state, illustrating the conforming nature of the inner side panels, and showing the outer side panels in a substantially horizontal orientation;

FIG. 10 is a view similar to FIG. 9, illustrating the next step in deploying the immobilizer, showing particularly the bending of the outer side panels in a downward direction such that the distal attachment panels can be secured adjacent the base to maintain the inner side panels in close conformity with the victim's head and to provide relatively rigid support therefor;

FIG. 11 is a partial, side elevational view of the assembled immobilizer of FIG. 10, illustrating the substantial access provided to the patient's ears in use;

FIG. 12 is a partial top plan view of the assembled head immobilizer of FIGS. 10 and 11, with the patient's head omitted for clarity of the details;

DETAILED DESCRIPTION OF THE INVENTION

Figure 13:
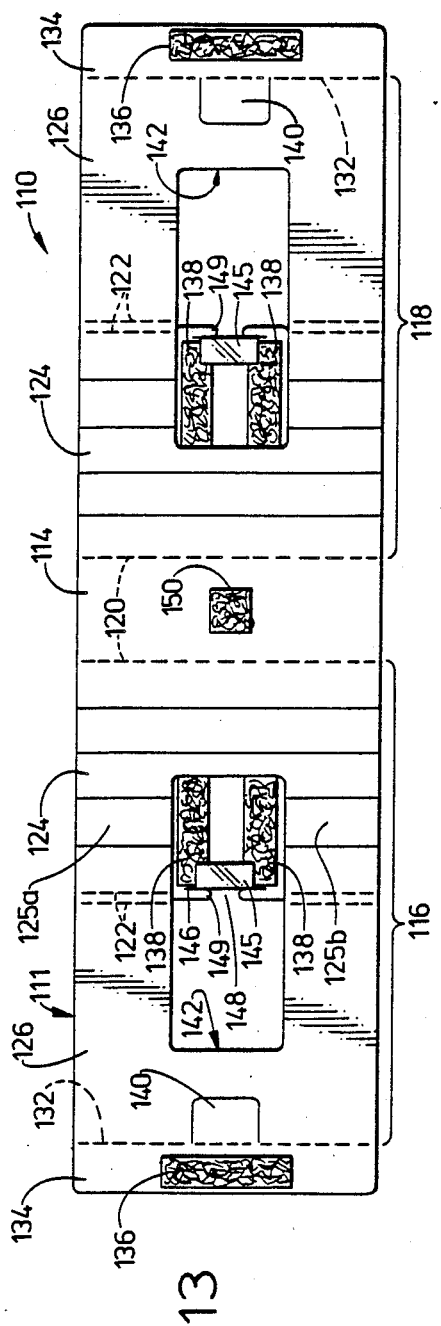
FIG. 13 is a top plan view of the upper surface of a blank illustrative of an alternate embodiment of an immobilizer of the present invention, shown in unassembled condition.

Referring now to the drawings in detail, wherein like numerals indicate the same elements throughout the views, FIGS. 1-12 are illustrative of a preferred embodiment of a head immobilizer 10 made in accordance with the subject invention. Particularly, FIG. 1 illustrates the upper or inner surface of a blank 11 cut to form a head immobilizer 10.

Blank 11 is preferably formed from a single piece of corrugated material, sheet plastic, cardboard, or similar low cost material which is light in weight and can be folded for storage and use. It is contemplated that manufacturing blank 11 of low cost material of this nature will facilitate the availability of an improved head immobilizer device to low budget emergency vehicle operations, and enable practical disposability of the unit after a single use. Blank 11 can preferably be manufactured by high speed automated machinery, thereby further reducing its overall production costs. While an immobilizer 10 could be reusable if made from plastic or corrugated material having a moisture resistant coating or the like, the low cost and simple construction of the present invention is designed to make the unit practical as a disposable unit for convenience and safety.

Immobilizer blank 11 comprises a center portion or base 14, preferably having a longitudinally extending rectangular center portion which will provide a flat area upon which a patient's head can be rested. Central longitudinal axis Z is shown in FIG. 1 as a reference for later discussions regarding the erection and use of immobilizer 10. Preferably, integrally formed with and extending laterally from the respective opposed lateral edges of base 14 along a pair of spaced score or bend lines 20 are side support panels 16 and 18. Score lines 20 hingedly attach side support panels 16 and 18 to their respective spaced lateral edges of base 14, and can be accomplished in any convenient manner, such as by spaced perforations, compression marking, or other known means of providing bend lines in materials. While it is preferred that score or bend lines 20 not fully traverse the entire longitudinal length of base 14, this is not critical to the present invention. The intermittent nature of bend lines 20 is preferred to maintain the strength and integrity of base 14 and the outwardly extending base extremity portions 30, as will be described.

As seen best in FIGS. 1 and 2, a pair of oppositely disposed, laterally extending flaps or extremities 30 are formed in blank 11 by the lines of severance shown at 31. A line of severance, as used herein, can be a line of weakness, such as cuts, perforations, slots, or the like, to provide separation of panels 30 from the adjacent blank material. As illustrated, the inner edges of flaps 30 preferably remain attached to base 14. Each side support panel (i.e. 16 and 18) includes an inner side panel 24 and an outer side panel 26. Lines of severance 31 are formed within inner panels 24 to enable separation of base extremities 30 from the adjacent portions of inner panels 24 upon deployment of the immobilizer, as will be set forth in greater detail below.

Attached in substantially the center of base 14 is a storage or securement device 50 for releasably holding the distal ends (e.g. securing flaps 34) of side support panels 16 and 18 in folded position for shipping and storage of an immobilizer device 10, as best illustrated in FIG. 4. As also shown in FIG. 1, a pair of longitudinally spaced attachment strips 38 are preferably provided on the upper outer surfaces of base extremities 30. Strips 38 are illustrated as complimentary hook-and-loop interlocking fabric pile strips for complimentary use with interlocking attachment strips 36 as will be explained.

The hook-and-loop interlocking strips, generally known in the art as "Velcro ™" are illustrated only as a preferred means for securing the outer panels 26 in a bracing position relative inner panels 24 as will be described below. The Velcro ™-type attachment arrangement is preferred to enable provision of dependable but adjustable securement of side support panels 16 and 18 in immobilizing position to enable medical personnel to optimally adjust the immobilizer 10 to a patient's head.

At the distal ends of extremities 30, there is preferably formed a slit 46 and an open area or access cutout 48 which effectively provide a pair of facing digits or fingers 49. It should be understood that immobilizer 10 is designed for attachment to the upper surface of a rigid backboard support (e.g. support 12 shown in FIG. 4). As illustrated in FIG. 2, the bottom surface of base 14 can be provided with a pair of pressure sensitive pads 44 having removable cover strips 45. Pads 44 are preferably mounted on the bottom surfaces of extremities 30 of base 14, as illustrated, to provide additional support for attachment procedures, as will be defined in greater detail below.

To attach immobilizer 10 to backboard 12, immobilizer 10 is oriented with its lower surface adjacent the upper surface of the backboard support, cover strips 45 are removed, and downward pressure on immobilizer 10 causes pressure sensitive pads 44 to hold the immobilizer in place on a backboard support. To simplify this attachment procedure, it is contemplated that cover strips 45 will preferably be doubled over upon themselves such that a free end (45a) can extend upwardly through slit 46 and above the upper surface of immobilizer 10. In this way, fingers 49 serve to hold the distal edge 45a of the protective strip 45 in an accessible position from the upper surface of immobilizer 10, such that a user can first align immobilizer 10 on the upper surface of a rigid backboard support 12, then merely pull upwardly on the distal ends 45a of the cover strips to expose the pressure sensitive pads 44 without moving the aligned immobilizer 10. It should be understood that alternate means for securing immobilizer 10 to a rigid support (e.g. hook and loop material arrangements) might also be preferred for immobilizers which are revised and must be adequately cleaned between uses.

Inner side panels 24 are hingedly connected at their inner edge to base 14 via score lines 20, and are hingedly connected at their outer edges to outer side panel 26 by a pair of parallel score lines 22. As will be understood, the parallel double score lines 22 enable bending of outer side panel 26 in either direction relative inner side panel 24, and further enabling folding of outer side panel 26 into face-to-face relationship with inner side panel 24 in storage position. FIG. 4 illustrates immobilizer 10 in such folded or storage position. As can be appreciated, the unique structure of the present invention enables its provision of a convenient folded position which features substantially uniform thickness to facilitate storage and shipping, and which is conveniently maintained by securement means (e.g. pad 50) to prevent damage to the immobilizer and interference with other equipment.

Inner side panels 24 further preferably include a plurality of parallel, spaced bend lines 28 to provide means for enabling inner panels 24 to closely conform to the shape of a patient's head being immobilized in the device. It is contemplated that bend lines 28 might not be necessary in immobilizers formed of flexible plastic or other similar material. As described above, it will be understood that the severance of extremities 30 from the inner portions of inner panels 24 provides an opening which effectively divides a substantial portion of inner panel 24 into a pair of spaced, inner support members (e.g. 25a and 25b). As will be seen, the openings formed by removal of extremities 30 from inner panels 24 provide substantial unencumbered access to the ears of a patient immobilized in the device.

Outer panels 26 have a substantially centrally located cutout portion 42 which can be removed during formation of blank 11, and preferably include a manipulation tab or handle 40 formed adjacent their distal edges. Manipulation tab 40 is to remain attached to blank 11 along score line 32, however, it is contemplated that the remaining three edges of tab 40 shall be formed by lines of severance to allow tab 40 to extend outwardly in use relative outer panel 26, as will be described below.

Hingedly attached adjacent the distal edge of each outer panel 26 is a securing flap 34 preferably having a Velcro TM strip 36 provided on its upper surface as a means for securing outer panel 26 in a bracing position relative inner panel 24 (e.g. as illustrated in FIGS. 10–12).

Following manufacture, blank 11 is folded from its flat condition shown in FIG. 1–3 to a folded or storage condition as seen best in FIGS. 4–7. Specifically, outer side panels 26 and their hingedly attached securing flaps 34 are folded inwardly about the double score lines 22 such that outer panels 26 are in face-to-face relationship with inner panels 24. It is preferred that securement pad 50 be provided for releasable engagement with attachment strips 36 of securing flaps 34 in order to hold the folded immobilizer 10 in storage position. Immobilizers 10 folded and maintained in such a storage position can be conveniently stacked for shipping and storage such that minimum space is occupied and chances of damage to the product are also largely obviated. As also illustrated in FIGS. 4–7, an immobilizer 10 in storage position can be easily attached to the upper surfaces of a backboard 12 for ready to use storage therewith, thereby ensuring that an immobilizer will be properly attached to and available for immediate use as needed with the backboard 12.

It should be noted that due to the unique structure of the subject immobilizer, the storage position provides a uniform thickness (i.e. only two layers of the blank 11 are sandwiched together) and the device does not extend beyond the lateral edges of a standard rigid backboard 12. These features are important in practical use, as they minimize inconvenience of storing an immobilizer 10 and/or a backboard support 12 having an immobilizer 10 attached thereto in stacked relationship with other units. Moreover, because immobilizer 10 does not extend beyond the lateral edges of the standard rigid backboards commonly used in the industry, chances for pre-use damage to the immobilizer can be minimized. An immobilizer 10 attached to a backboard support 12 will also not interfere with use of the backboard where head immobilization is not required, and generally provides a pad for a patient's head in any case.

FIGS. 8–12 illustrate deployment of immobilizer 10 once it has been attached to a backboard 12. In particular, side support panels 16 and 18 are first bent upwardly along score lines 20 as shown in FIG. 8. As illustrated in FIG. 9, panel bend lines 28 enable the inner side panels 24 to closely conform to the sides of a patient's head to be immobilized. As understood from the discussion above, and as illustrated in FIGS. 8–12, base portion extremities 30 remain in planar relationship with the upper surface of backboard 12 and an opening is provided in inner panel 24 to provide substantial access to the ears of a patient therewithin.

While holding the patient's head still, inner side panels 24 are bent to conform closely with the patient's head, then, as illustrated in FIG. 10, outer side panels 26 are bent downwardly and securing flaps 34 are bent inwardly for attachment in bracing position. As illustrated in FIG. 9, upon bending securing flaps 34 inwardly, it will be understood that manipulation tabs 40 will extend outwardly along score line 32 to provide a convenient grasping handle for the user to facilitate attachment and adjustment of outer panels 26 in bracing position. As seen best in FIG. 10, cutout 42 of outer side panels 26 aligns with the opening formed in inner panels 24 to provide substantially unencumbered access to the patient's ears in use.

FIG. 12 has been provided to illustrate another advantage of the subject invention for providing enhanced support and comfort to a patient's head. In particular, as described above, the opening formed in inner panels 26 effectively provides a pair of spaced inner support members (e.g. 25a and 25b) hingedly connected to base 14 along score line 20. It has been found that the inner support members 25a and 25b can be effectively independently adjustable to more closely conform to a shape necessary to optimally support a patient's head. An anatomical fact is that the human head is generally tapered from top to bottom. Consequently, in order to most comfortably and effectively support the human head, an immobilizing device must be adjustable in several directions. The pair of spaced support members of immobilizer 10 can better conform to a patient's head because they can be effectively independently manipulated along a three dimensional tri-ordinate system (i.e. along three axes of movement as seen best in FIGS. 9 and 12 along the X, Y and Z axes, providing almost infinite adjustability as well as enhanced support and comfort.

As illustrated in FIG. 12, manipulation tabs 40 extend outwardly to enable easy adjustment of the orientation of outer side panels 26 and their hingedly attached securing flaps 34 relative longitudinal axis Z. By providing an enlarged area of attachment (e.g. by providing longitudinally spaced strips 38) securing flaps 34 can be firmly secured in any of a variety of positions to enable selective and custom conformation of inner panels 24 to a patient's head. It is contemplated that spaced strips 38 could be equally substituted by a rectangular hook and loop pad to provide a sufficient area of attachment for flaps 34 in a variety of positions. The top view of FIG. 12 illustrates the angular orientation of outer panels 26 relative longitudinal axis Z which might be required to conform to the typical taper and other irregularities of the human head. Once the patient's head is snugly enclosed and supported within immobilizer 10 as described, it may also be preferred to complete immobilization by securing the erected immobilizer 10 and the patient's supported head by adhesive tape or other strapping method (e.g. velcro straps or the like) to the backboard support as a unit. A typical strapping arrangement would span across the patient's forehead and around either side of the immobilizer around opposite sides of the backboard support, as is well known in the industry.

Figure 14:
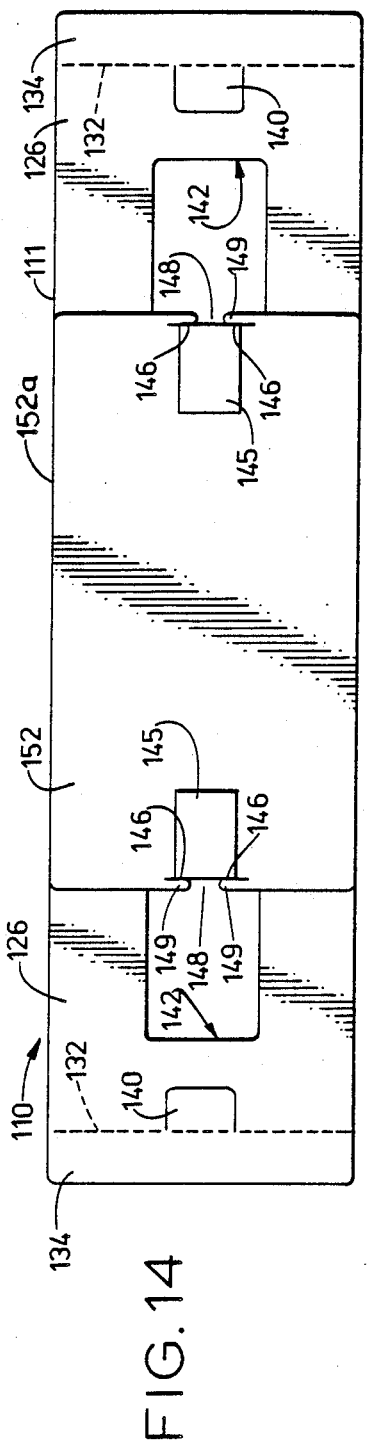
FIG. 14 is a plan view of the bottom surface of the immobilizer of FIG. 13.
Figure 15:
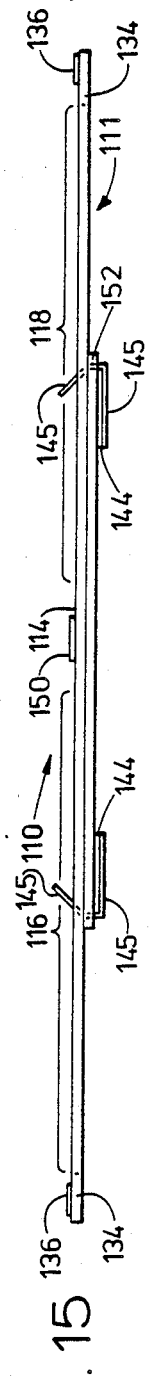
FIG. 15 is a front elevational view of the immobilizer blank shown in FIG. 13.

FIGS. 13-15 illustrate an alternate preferred embodiment of a head immobilizer 110 made in accordance with the subject invention. Like elements of this alternate embodiment are illustrated and identified with numbers having identical last two digits as the corresponding elements shown in FIGS. 1-12. For example, the inner side panels 124 are substantially identical to inner sides 24 of FIG. 1, and are identified by a number having the same last two digits (i.e. 24).

Blank 111 shown in FIG. 13, however, differs from blank 11 of FIG. 1 in that only a portion of inner panels 124 has been cut out to form the spaced inner support members 125a and 125b. In particular, it is contemplated that a single cutout (e.g. 142) traversing portions of both and panels 124 and outer panels 126 can be provided in blank 111 as a rectangular opening having the material removed therefrom. Unlike the embodiment shown in FIG. 1, only a portion of inner panels 124 is effectively separated into independent support members 125a and 125b, with the portion closest to base 114 remaining as a single longitudinally extending unit. In this regard, the lower areas of inner panels 124 would conform to the portions of the patient's head closest to the rigid backboard support, while the spaced inner support panels 125a and 125b could be substantially independently fit in conformance with the upper portions of the patient's head adjacent the ears.

As seen best in FIGS. 14 and 15, a second blank of material 152 is contemplated as being secured to the lower surface of blank 111 adjacent its central portions. It is contemplated that the lower blank of material 152 will be adhered or otherwise connected to the lower portions of base 114, and should not be connected to any portion of the side panels 116 or 118, as these portions must be relatively free to conform to the patient's head and to support the same. As also illustrated in FIGS. 13 and 14, the upper surfaces of sheet member 152 would also preferably include the pair of spaced Velcro TM pile strips 138, or similar means, for attaching securing flaps 134 and outer panels 126 in bracing relationship to inner panels 126 in use. The second sheet of material 152 would include similar means for attaching immobilizer 110 to a backboard support (e.g. pressure sensitive pads 144 or hook and loop arrangements) as described above with regard to immobilizer 10.

It is contemplated that the two-part construction shown in FIGS. 13-15 might simplify manufacturing procedures, such as cutting and removing portions of the material blanks. In particular, the formation of the ear openings and the various base extremity members might be more easily accomplished without complex equipment. Immobilizer 110 would, consequently, include one extra layer of material in its folded or storage condition, but otherwise would be used in substantially the identical manner as described above. It should also be understood that immobilizer 110 of FIGS. 13-15 could equally be formed from a single blank of material, and simply folded into the configuration shown. For example, lower blank 152 could be attached to blank 111 along either of their common lateral edges by means of a fold line (e.g. 152a) which would enable blank 152 to be folded under blank 111.

Having shown and described the preferred embodiment of the present invention, further adaptions thereof can be accomplished by appropriate modification by one of ordinary skill in the art without departing from the scope of the present invention. For example, while the means for securing the inner panels in a desired immobilizing position have been illustrated and described as including interacting Velcro TM strips, it is contemplated that other attachment means and devices could equally be substituted. Also, as mentioned above, the particular material from which the immobilizer of the present invention is manufactured is not critical, and may differ according to customer preference, climates in which the immobilizer is to be used, preference as to whether the device is to be disposed or not, and other variables. Similarly, the immobilizer might be formed in a variety of sizes to better respond to particular applications. Accordingly, the scope of the present invention should be considered in terms of the following claims, and is understood not to be limited to the details of structure and function shown and described in the specification and drawings.

I claim:

1. A head immobilizer of the type which can be attached to a support backboard, said immobilizer comprising:

a base;

a pair of laterally extending side panels, each side panel further comprising an inner panel and an outer panel, said inner panel having means for conforming appropriately to a shape necessary to snugly support a head to be immobilized, said inner panel further comprising an opening which effectively divides a portion of said inner panel into a pair of spaced inner support members, said outer panel having inner and outer edges and being hingedly attached adjacent its inner edge to said inner panel and foldable relative to said inner panel to provide a substantially rigid brace for securing said inner panel in a desired immobilizing position, said outer panel comprising means for providing substantial access to said opening when said inner panel is braced in a desired immobilizing position; and means for securing said outer panel in a bracing position to support said inner panel in a desired immobilizing position, said securing means further comprising an attachment panel hingedly attached adjacent said outer edge of said outer panel and means for attaching said attachment panel adjacent said base.

2. The head immobilizer of claim 1, wherein said means for securing provides for selective attachment of said attachment panel in any of a plurality of orientations relative said base, whereby the conformation of said inner panel to the shape necessary to support a particular head can be adjusted by attachment of said attachment panel in an orientation to maintain said spaced inner support members in a desired position relative one another.

3. The head immobilizer of claim 1, wherein the hinged attachment of said outer panel to said inner panel also enables the folding of said outer panel and its attachment panel into an overlying relationship relative its corresponding inner panel such that said immobilizer can be folded into a substantially flat folded storage position.

4. The head immobilizer of claim 1, further comprising a manipulation tab adjacent said outer edge of said outer panel to provide for convenient manipulation of said side panel and adjustment of the conformation of said inner panel during attachment of the attachment panel.

5. The head immobilizer of claim 1, wherein said opening in said inner panel extends laterally across the central area of said inner panel effectively dividing a portion of said inner panel into a pair of spaced inner support members having first and second ends, said first ends being hingedly connected to said base, and said second ends being hingedly connected to the inner edge of said outer panel, said support members being substantially independently adjustable for conformance to a shape necessary to snugly support a head to be immobilized.

6. The head immobilizer of claim 1, wherein said immobilizer is formed from a unitary blank of material, and wherein portions of said material are cut out to form said openings in said inner panels and remain attached to said base to form laterally extending base extremities upon which said respective attachment panels may be attached when said outer panels are placed in bracing position.

7. The head immobilizer of claim 6, wherein said base extremities further comprise a pair of spaced securement strips to provide a pair of spaced attachment areas for said attachment panel, whereby said attachment panel can be reliably secured in a plurality of orientations to enable selective adjustment of the spaced inner panel support members to conform to a desired shape.

8. The head immobilizer of claim 5, wherein said opening extends laterally across substantially the entire inner panel.

9. The immobilizer of claim 1, wherein said base further comprises an upper base sheet forming a central base from which said side support panels extend, and a lower base sheet attached to the underside of said upper base sheet.

10. The immobilizer of claim 4, wherein said manipulation tabs are each formed integrally with the associated outer panel such that said tab can be folded outwardly from said outer panel in use.

11. The immobilizer of claim 1, wherein said means for providing substantial access to said opening in said inner panel comprises a cutout portion formed in said outer panel generally located so as to be aligned with said opening when said immobilizer is erected for immobilization of a patient's head.

12. An improved head immobilizer for use with a rigid support backboard, said immobilizer being formed from an integral blank of material and further comprising:
a centrally located base which can be attached to a support backboard, said base having a pair of laterally extending attachment flaps;
a pair of oppositely disposed side support panels, said side support panels extending laterally from opposite lateral edges of said base and hingedly attached thereto, said side support panels each further comprising an inner panel and an outer panel, said inner panel having means for conforming appropriately to a shape necessary to snugly support a head to be immobilized, said inner panel further comprising an opening which effectively divides a substantial portion of said inner panel into a pair of spaced inner support members, said outer panel having inner and outer edges and being hingedly attached adjacent its inner edge to said inner panel and foldable relative said inner panel to provide a substantially rigid brace for securing said inner panel in a desired immobilizing position, said outer panel comprising means for providing substantial access to said opening when said inner panel is braced in a desired immobilizing position; and
means for securing said outer panel in a bracing position relative said inner panel, said securing means further comprising an attachment panel hingedly attached adjacent said outer edge of said outer panel, and means for adjustably attaching said attachment panel to said attachment flaps of said base.

13. The head immobilizer of claim 12, wherein said means for securing provides for selective attachment of said attachment panel in any of a plurality of orientations relative said base, whereby the conformation of said inner panel to the shape necessary to support a particular head can be adjusted by attachment of said attachment panel to said attachment flap in a selected orientation to maintain said spaced inner support members in a desired position relative one another.

14. The head immobilizer of claim 13, wherein said means for securing further comprises a pair of spaced attachment strips on the upper surface of each of said attachment flaps for adjustably securing said attachment panels in a desired orientation.

15. The head immobilizer of claim 12, further comprising a manipulation tab adjacent the outer edge of each of said outer panels to provide for convenient manipulation of said side support panels and adjustment of the conformation of said inner panel during attachment of the attachment panel in use.

16. The immobilizer of claim 15, wherein said manipulation tabs are each formed integrally with the associated outer panel such that it can be folded outwardly from said outer panel in use.

17. The head immobilizer of claim 12, wherein said opening in said inner panel extends laterally across the central area of said inner panel effectively dividing a portion of said inner panel into a pair of spaced inner support members having first and second ends, said first ends being hingedly connected adjacent said base, and said second ends being hingedly connected to the inner edge of said outer panel, said support members being substantially independently adjustable for conformance to a shape necessary to snugly support a head to be immobilized.

18. The head immobilizer of claim 12, wherein said opening extends laterally across substantially the entire inner panel.

19. A head immobilizer of the type which can be attached to a rigid support backboard, said immobilizer comprising:
a first blank of material having a centrally located base and a pair of side support panels extending laterally from opposite lateral edges of said base and hingedly attached thereto, said side support panels each further comprising an inner panel and an outer panel, said inner panel having means for conforming appropriately to a shape necessary to snugly support a head to be immobilized, said side support panels each further comprising a cutout opening which effectively divides a substantial portion of said inner panel into a pair of spaced inner support members, said outer panels each having inner and outer edges and being hingedly attached adjacent its inner edge to said inner panel and foldable relative said inner panel to provide a substantially rigid brace for securing said inner panel in a desired immobilizinq position, said outer panel comprising means for providing substantial access to said opening when said inner panel is braced in a desired immobilizing position;

means for securing said outer panel in a bracing position to support said inner panel in a desired immobilizing position, said securing means further comprising an attachment panel hingedly attached adjacent said outer edge of said outer panel; and a second blank of material attached to the underside of said base of said first blank, said second blank having means for attaching said immobilizer to a support backboard, and having a pair of laterally extending attachment flaps and means for adjustably attaching said attachment panel to said attachment flaps in a desired bracing position.

20. The immobilizer of claim 19, wherein the cutout opening of said first blank extends across only the upper portion of said inner panel, providing a pair of spaced support panel members which can be adjusted effectively independently of one another to conform to the shape of a head to be immobilized.

21. The immobilizer of claim 19, wherein the cutout opening of said first blank extends across portions of both the inner and outer support panels, thereby providing ear access openings in said immobilizer when in immobilizing position.

22. A method for immobilizing the head of a patient lying on a rigid backboard support, said method comprising the following steps:

attaching a head immobilizer device to the upper surface of a rigid backboard support, said immobilizer device comprising a base, a pair of laterally extending side panels, each side panel further comprising an inner panel and an outer panel, said inner panel having means for conforming appropriately to a shape necessary to snugly support a head to be immobilized and further comprising an opening which effectively divides a substantial portion of said inner panel into a pair of spaced inner support members, said outer panels each having inner and outer edges and being hingedly attached adjacent its inner edge to said inner panel and foldable relative said inner panel to provide a substantially rigid brace for securing said inner panel in a desired immobilizing position, said outer panel comprising means for providing substantial access to said opening when said inner panel is braced in a desired immobilizing position, and means for securing said outer panel in a bracing position relative said inner panel, said securing means further comprising an attachment panel hingedly attached adjacent said outer edge of said outer panel, and means for attaching said attachment panel adjacent said base;

placing a patient's head on the base of the immobilizer device;

bending the laterally extending side support panels of said immobilizer device upwardly around the patient's head such that said inner panels snugly conform to the lateral sides of the patient's head; and bending the outer panels downwardly and outwardly and securing the attachment panels adjacent the base to brace said inner panels in snug conformance with the patient's head in immobilized position, whereby the patient's head is immobilized yet substantial access is provided to the patient's ears through the openings in said side support panels.

23. The method of claim 22, further comprising the step of adjusting the orientation at which said attachment panels are secured adjacent said base to effectively independently adjust the conformance of each of said inner support members to optimize the support and comfort of the patient's head.

* * * * *